(12) United States Patent
Moulton et al.

(10) Patent No.: US 6,740,678 B2
(45) Date of Patent: May 25, 2004

(54) METHOD OF TREATMENT OF CARDIOVASCULAR INJURIES

(75) Inventors: Karen S. Moulton, Weston, MA (US); Judah Folkman, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 126 days.

(21) Appl. No.: 09/822,765

(22) Filed: Mar. 30, 2001

(65) Prior Publication Data

US 2002/0006895 A1 Jan. 17, 2002

Related U.S. Application Data

(63) Continuation of application No. PCT/US99/22902, filed on Oct. 1, 1999.
(60) Provisional application No. 60/102,616, filed on Oct. 1, 1998.

(51) Int. Cl.$^7$ .............................................. C07C 403/00
(52) U.S. Cl. ........................... 514/475; 560/1; 568/579; 568/626; 568/670
(58) Field of Search ..................... 514/2, 475; 568/579, 568/626, 670; 560/1

(56) References Cited

U.S. PATENT DOCUMENTS 5,112,946 A * 5/1992 Maione ...................... 530/324
5,290,807 A    3/1994 Folkman et al. ............. 514/575
5,698,586 A   12/1997 Kishimoto et al. .......... 514/475
5,800,820 A *  9/1998 Maione .................... 424/198.1
5,830,879 A   11/1998 Isner ........................... 514/44
5,837,682 A * 11/1998 Folkman et al. .............. 514/12
5,854,205 A * 12/1998 O'Reilly et al. ................ 514/2

OTHER PUBLICATIONS

Lazarous et al., "Comparative Effects of Basic Fibroblast Growth Factor and Vascular Endothelial Growth Factor on Coronary Collateral Development and the Arterial Response to Injury," Circulation vol. 94(5), pp. 1074–1082, 1996.
Nabel et al., "Recombinant fibroblast growth factor–1 promotes intimal hyperplasia and angiogenesis in arteries in vivo," Letters to Nature vol. 362, pp. 844–846, 1993.

* cited by examiner

Primary Examiner—Christopher S. F. Low
Assistant Examiner—David Lukton
(74) Attorney, Agent, or Firm—Nixon Peabody LLP

(57) ABSTRACT

The present invention provides a method for treating cardiovascular ailments. The method involves first screening an individual to determine their risk of having the potential for unstable plaques. Such individuals can be selected by looking at one of the following criteria: (i) increased plaque neovascularization, (ii) area ratio of intima to wall area of a plaque, (iii) evidence of plaque hemorrhage, or (iv) inflammatory cells associated with plaque vessels. Looking at these criteria permits one to select individuals having the potential for unstable plaques. The method then involves treating the selected individual with an effective amount of an angiogenesis inhibitor.

3 Claims, 6 Drawing Sheets

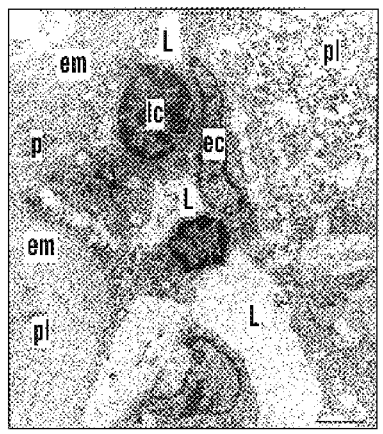 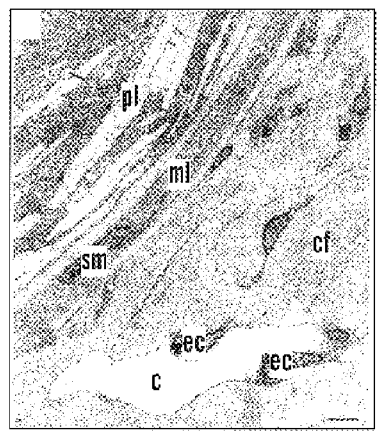 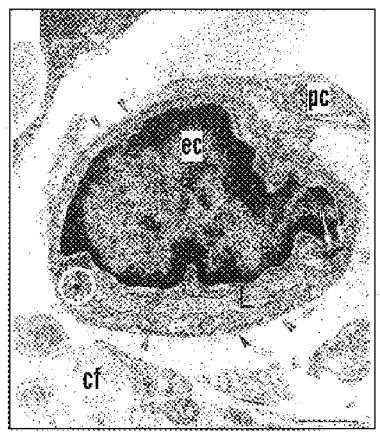
*FIG. 2A*     *FIG. 2B*     *FIG. 2C*

METHOD OF TREATMENT OF CARDIOVASCULAR INJURIES

This application is a continuation of copending International Application PCT/US99/22902, filed Oct. 1, 1999, and which designated the U.S. The non-provisional application designated above, namely PCT/US99/22902, filed Oct. 1, 1999, claims the benefit of U.S. Provisional Application No. 60/102,616, filed Oct. 1, 1998.

The present invention is directed to a method for treatment of cardiovascular injuries where plaque formation is present. The method involves administering an angiogenesis inhibitor to the plaque.

BACKGROUND OF THE INVENTION

Cardiovascular ailments are a significant problem in society. Individuals afflicted with them can have decreased mobility, can require prolonged administration of drugs and the conditions can lead to death. These ailments can include atherosclerosis, restenosis, thrombosis, myocardial infarction, coronary heart disease, stroke, and other diseases.

Atherosclerosis is a common form of arteriosclerosis that results from the development of an intimal lesion and subsequent narrowing of the vessel lumen. As the lesions increase in size, they reduce the diameter of the arteries and impede blood circulation. The formation of the atherosclerotic lesion is typically classified in five overlapping stages—(1) migration of smooth muscle cells, (2) lipid accumulation, (3) recruitment of inflammatory cells, (4) proliferation of vascular smooth muscle cells, and (5) extracellular matrix deposition. In a healthy vessel, the vast majority of the smooth muscle cells are contained in the vessel media. As lesions develop, smooth muscle cells migrate from the media to the intima of the vessel. Although smooth muscle cells in healthy vessel walls do not significantly accumulate lipid, the intimal smooth muscle cells have an increased capacity for lipid uptake and storage. One model of lesion progression proposes that macrophages are attracted to the lipid accumulating in the lesions in order to remove the lipid from the vessel wall. Moreover, the intimal smooth muscle cell accumulation is typically accompanied by medial thinning. These lesions are also rich in extracellular matrix deposition, particularly collagen fibers.

In some advanced lesions, new capillaries grow into the inner intimal layer of the plaque. The vasa vasorum are small nutrient arteries and veins found in the media and adventitia of larger blood vessels. In vessels containing artherosclerotic lesions, this microvascular network can become more abundant and extend into the intima (sometimes referred to here as plaque vessels or intimal vessels).

There are presently a number of methods for treating atherosclerosis, which include both surgical and medical treatment. The therapy that is presently preferred is percutaneous translumenal coronary angioplasty ("PTCA", commonly referred to as "balloon angioplasty"). In this procedure, a catheter equipped with an inflatable balloon is threaded intravascularly to the site of the atherosclerotic narrowing of the vessel. By inflating the balloon, the plaque enlarging the vessel is compressed, thereby reducing the obstruction and improving coronary flow. Thus, this procedure is widely used in patients with coronary artery disease, particularly to relieve myocardial ischemia.

While the initial success appears high, complications can frequently develop. For example, stenosis following this procedure remains a significant problem with a significant number of patients, in some studies up to one-third of the patients, developing restenosis within one to three months. Restenosis refers to the renarrowing of an artery after initially successful angioplasty. Restenosis of the blood vessel is thought to be due to injury to the endothelial cells of the blood vessel during angioplasty or during the inflation of the balloon catheter. During recovery after surgery, smooth muscle cells proliferate faster than endothelial cells narrowing the lumen of the blood vessel and narrowing the atherosclerotic process anew. Accordingly, in recent years such smooth muscle cell proliferation has been recognized as a major clinical problem limiting the effectiveness of percutaneous translumenal coronary angioplasty.

There have been numerous attempts to deal with this problem. For example, using a double balloon catheter for regional delivery of a therapeutic agent at the angioplasty site, such as heparin. Another approach has been to place endovascular stents in the dilated segments to mechanically block abrupt closure and restenosis. However, the use of such stents is limited by direct (subacute thrombosis) or indirect (bleeding, peripheral vascular complications) complications. Other approaches include treating the patient with anticoagulant and/or antiplatelet agents during the recovery period.

Recently the use of angiogenic agents has been proposed to assist in recovery. See e.g. U.S. Pat. No. 5,830,879. This patent teaches that by using an angiogenic agent, such as vascular endothelial growth factor (VEGF), smooth muscle cell proliferation is indirectly inhibited by the agent, directly facilitating reendothelization of the injured vessel. Angiogenic agents have also been proposed for treatment of other vascular problems. However, the long-term prognosis of the patients treated by this approach is not known. For example, published studies have demonstrated that delivery of endothelial cell growth factors, such as VEGF and members of the FGF family (FGF-1, FGF-2), to the vessel wall have been accompanied by increased intimal thickening at the site of vascular balloon injury. (Lazarous, D. F., *Circulation* 94: 1074–82, 1996; Nabel, E. G., *Nature* 362: 844–6, 1993). Accordingly, the need for other methods to reduce problems associated with artherosclerosis and angiogenesis remain. In addition, patients with current malignancies and retinal neovascularization are currently ineligible for treatments with angiogenic agents, but may be appropriate candidates to receive angiogenesis inhibitors.

SUMMARY OF INVENTION

We have now discovered that by delivering angiogenesis inhibitors to patients having coronary diseases where there is an increase in plaque vessels, we can inhibit plaque growth and reduce intimal neovascularization and inhibit lesion severity.

The angiogenesis inhibitor can be delivered by using the agent itself or a nucleic acid segment encoding the appropriate agent. The angiogenesis inhibitor can be selected from the group consisting of fumagillin derivatives such as O-chloracetyl-carbamoylfumagillol (sometimes called AGM-1470 or TNP-470), endostatin (a C terminal 20 kd fragment of the basement membrane protein Collagen XVIII; Ingber, B., et al., *Nature* 348: 555–7, 1990; Boehm, T., et al., *Nature* 390, 404–7, 1997; O'Reilly, M. S., et al., *Cell* 88: 277–85, 1997), angiostatin, platelet factor 4, vasostatin, interferon-α and -β (IFN), thalidomide, thrombospondin peptides, etc. TNP-470 and endostatin are preferred.

In this method one selects an individual showing signs of a coronary vascular problem such as formation of an atherosclerotic lesion. Preferably one screens the individual for an assessment of plaque vessel growth, unstable clinical symptoms, or evidence of increased neovascularization in atherosclerotic lesions. We have found that it is the unstable plaque vessels that can cause the greatest trauma to the individual. The plaques can be determined by looking at the degree of neovascularization or evidence of intramural hemorrhage or for the presence of inflammatory cells. We believe capillaries in the intimal layer of atherosclerotic lesions are permeable and mechanically weak, which predisposes them to bleed. The degree of neovascularization in atherosclerotic lesions is correlated with areas of high inflammatory cell content. Areas of inflammatory cells in some lesions are sites of mechanical weakness and correspond to sites of plaque rupture, which trigger thrombosis in the artery and give rise to heart attacks, strokes and vascular occlusion (Burke, A. P., *New Engl. J. Med.* 336:1276–82, 1997).

Although the capillaries within atherosclerotic lesions are too small to be detected by conventional angiography, the detection of intimal neovascularization in atherosclerotic lesions may be accomplished by known methods such as magnetic resonance imaging with contrast agents that show enhancement in tissues with increased perfusion and permeability; nuclear scintigraphy of lesions that show accumulation of technetium-99m labeled agents that target endothelial cells and/or inflammatory cells in lesions; and by intravascular, duplex, and conventional ultrasound used in conjunction with blood contrast agents (Vallabhajosula, S., J., *Nuclear Med* 38: 1788–96, 1997). Newly developed technologies such as optical coherence tomography (OCT) and infrared or rahman spectroscopy can be enhanced to detect target molecules associated with the endothelial cells that comprise plaque neovascularization or evidence of hemorrhage around the neovascularization in the plaque.

Looking at plaque thickness is an alternative for screening for unstable plaques. In our studies, we found that increased plaque thickness beyond 250 microns, or about 0.3 mm thickness, was associated with a 9-fold increased prevalence of intimal neovascularization in atherosclerotic lesions in mice. This dimension is observed in human atherosclerotic lesions also (Geiringer, E., *J. Pathol. Bact.* 63: 210–11, 1951). Another criteria is measuring the intima area to total wall area of the plaque, by intravascular ultrasound for example. If the area ratio is at least 0.4, preferably about 0.5, more preferable 0.54 or greater, then the plaque is considered potentially unstable and the individual is selected for treatment.

After an individual is selected, the individual is treated by administration of the angiogenesis inhibitor. In one embodiment one administers a nucleic acid sequence encoding an angiogenesis inhibitor, instead of the agent.

The plaque may be contacted with the agent by any means of administration. For example, subcutaneous injection of the agent, oral administration, or injection by a catheter or needle. One preferred method is by use of standard catheter delivery systems to bring the agent to the general region where the plaque is present. These methods include use of aorta balloon catheter, porous balloon catheter, and a hydrophilic polymer coated balloon such as a hydrogel polymer coated balloon.

The term "effective amount" means the amount necessary on the part of the agent or the nucleic acid delivered to the plaque cells in the lesion to inhibit plaque growth.

BRIEF DESCRIPTION OF THE FIGURES

FIG. 1A shows a lesion from the descending aorta that shows vessels in the intima identified by antibodies against CD31 (100×). FIG. 1B. Higher magnification (25×) of the inset region shows multiple capillaries. FIG. 1C. Marked intimal neovascularization detected by antibodies to CD31 is located near the medial layer in a separate lesion (400×). FIG. 1D. Intimal vessels in this plaque appear to run perpendicular to the media. FIG. 1E. An intimal capillary (large arrow), which extends along the intima-medial border (small arrow), is identified by antibodies to vWF. FIG. 1F. Atherosclerotic plaque at the aortic origin shows a large capillary-like vessel (large arrow) that is filled with red blood cells and identified by antibodies against vWF. Bar at 400× represents 20 microns.

FIGS. 2A–2C show transmission electron microscope images of intimal and adventitial vessels associated with lesions in Apo E-/-mice. FIG. 2A. Cross-section through a plaque (pl) in the lower thoracic aorta. An intimal vessel is located adjacent to the elastic membrane (em) of the aortic wall. The capillary lumen (L) contains lymphocytes (lc) that are in close contact to the endothelial cell (ec) and platelets (p) with alpha granules. Bar=2Tm. FIG. 2B. Periaortic vessels in the adventitia associated with an atherosclerotic plaque. The medial layer (ml) with smooth muscle cells (sm) is eroded by the plaque (pl) to a thickness of about 6 Tm. The lacunar capillary (c) that is comprised of two endothelial cells (ec) is void of pericytes. cf=collagenous fiber bundles. Bar=5 Tm. FIG. 2C. Capillary sprout in the adventitial layer of lesion shown in FIG. 2B. Two endothelial cells interconnected by punctiform (circled) and more complex cell contacts (arrow) form an early lumen (L) filled with amorphous substance.

Arrowheads point to the basal lamina and large numbers of pinocytotic vesicles. The extensions of the pericytic cell (pc) have not yet reached the presumed newly formed vessel. Bar=1 Tm.

Figure 3:
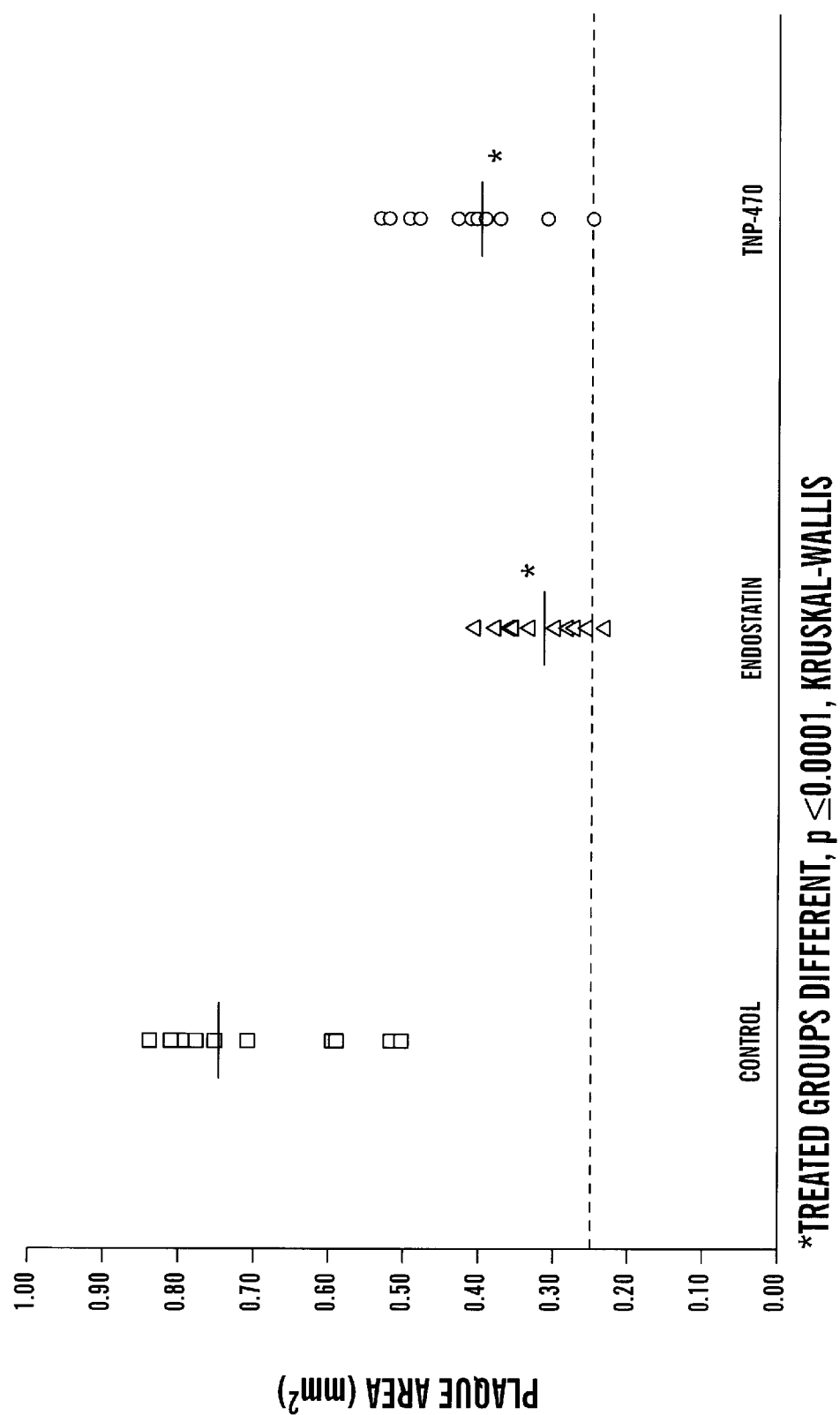

FIG. 3 shows size of lesions at the aortic origin after treatment with angiogenesis inhibitors from age 20 to 36 weeks. Control (square), endostatin (triangle), and TNP-470 (circle) animals were treated for 16 weeks as described in Methods. Dashed line centered at 0.25 mm$^2$ represents the median plaque area of aortic sinus lesions measured in a cohort (N=10) analyzed at 20 weeks.

Figure 4:
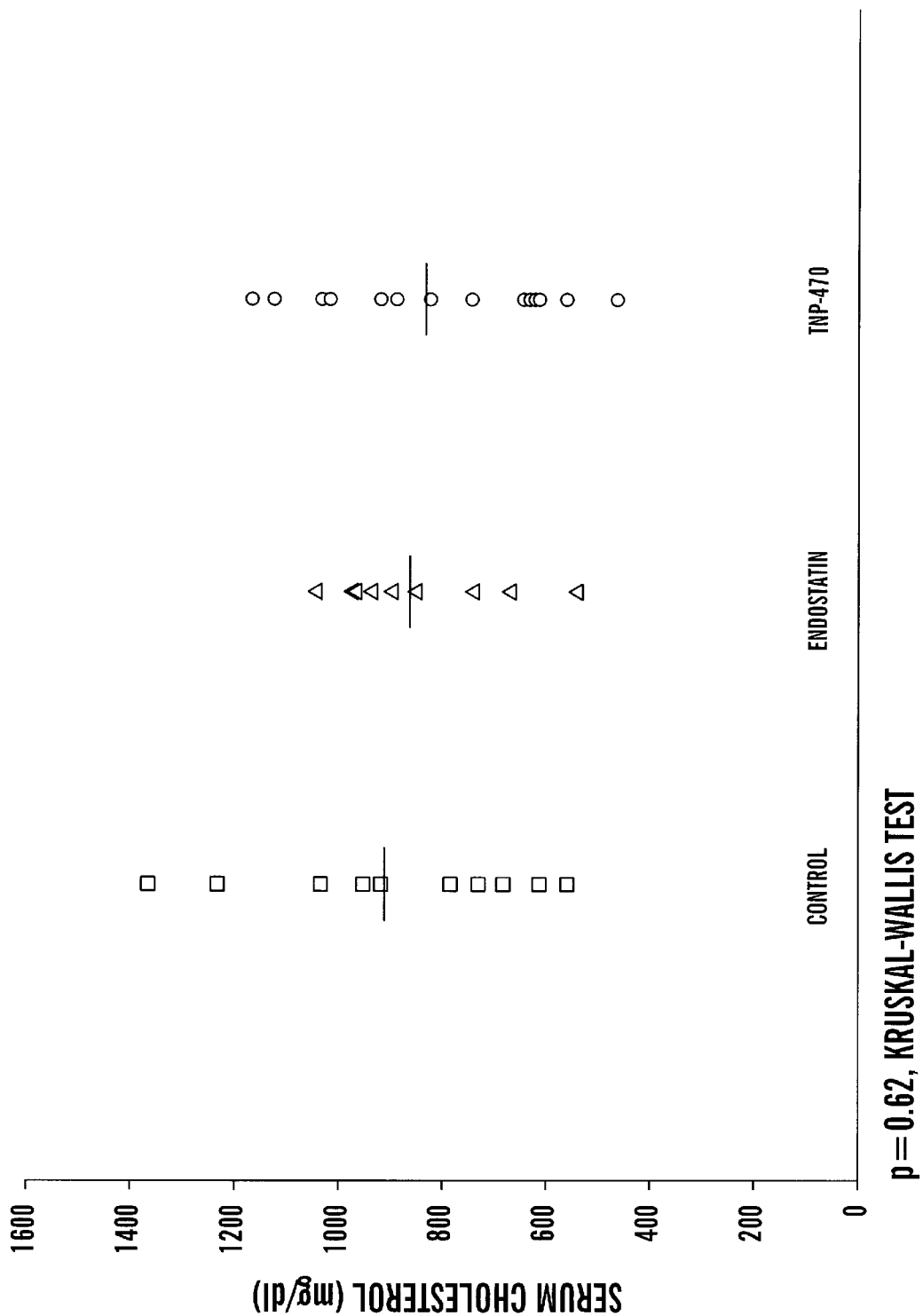

FIG. 4 shows serum cholesterol levels. Blood samples were collected at 36 weeks from controls (square) and animals treated with endostatin (triangle) or TNP-470 (circle). Inhibition of atherosclerotic lesions by angiogenesis inhibitors occurred by mechanisms independent of effects on serum cholesterol.

Figure 5:
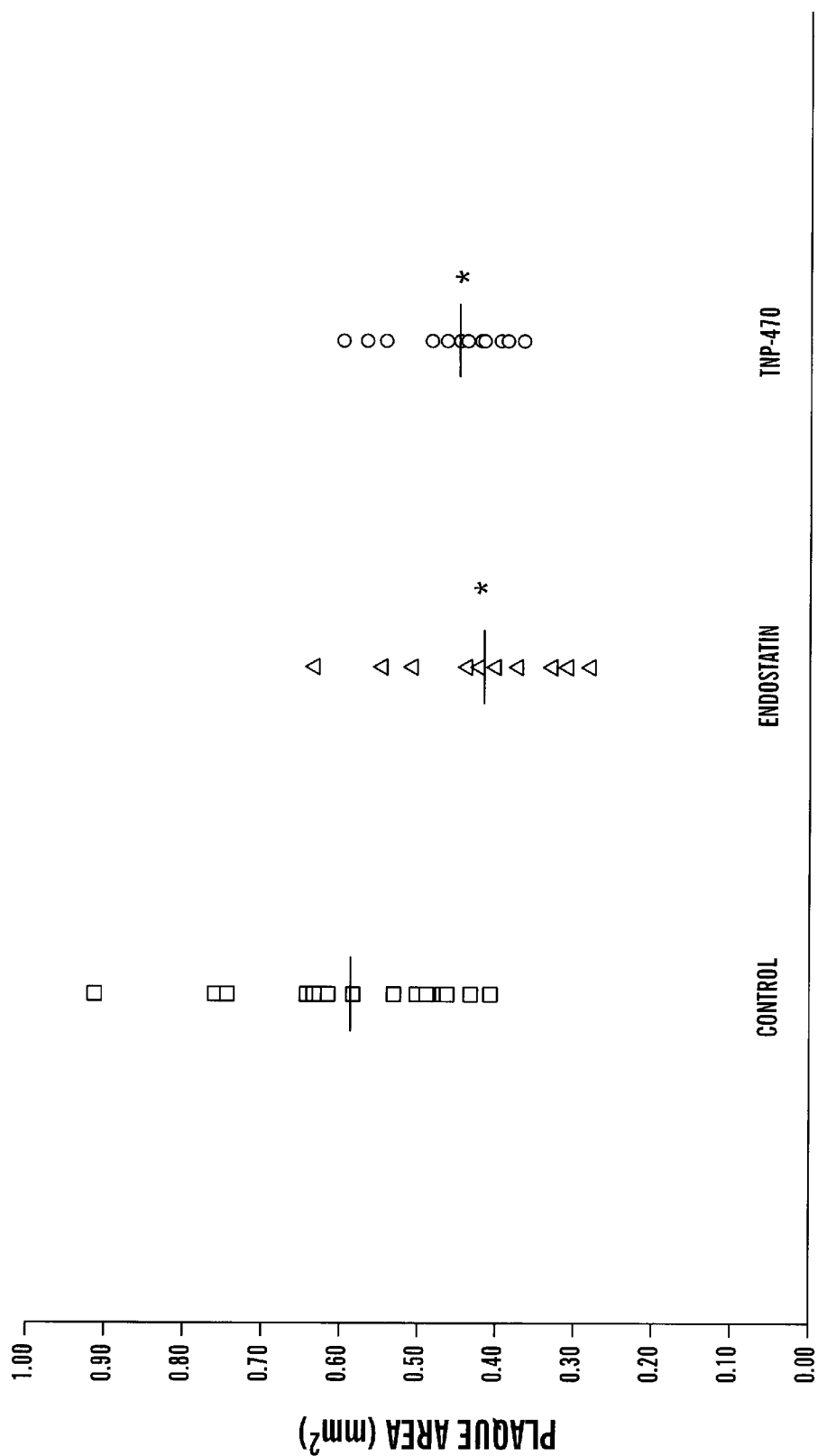

FIG. 5 shows size of lesions at the aortic origin after treatment with angiogenesis inhibitors from age 32 to 48 weeks. Median plaque areas for endostatin (triangle) and TNP-470 (circle) treated Apo E-/-mice are reduced compared to controls.

Figure 6:
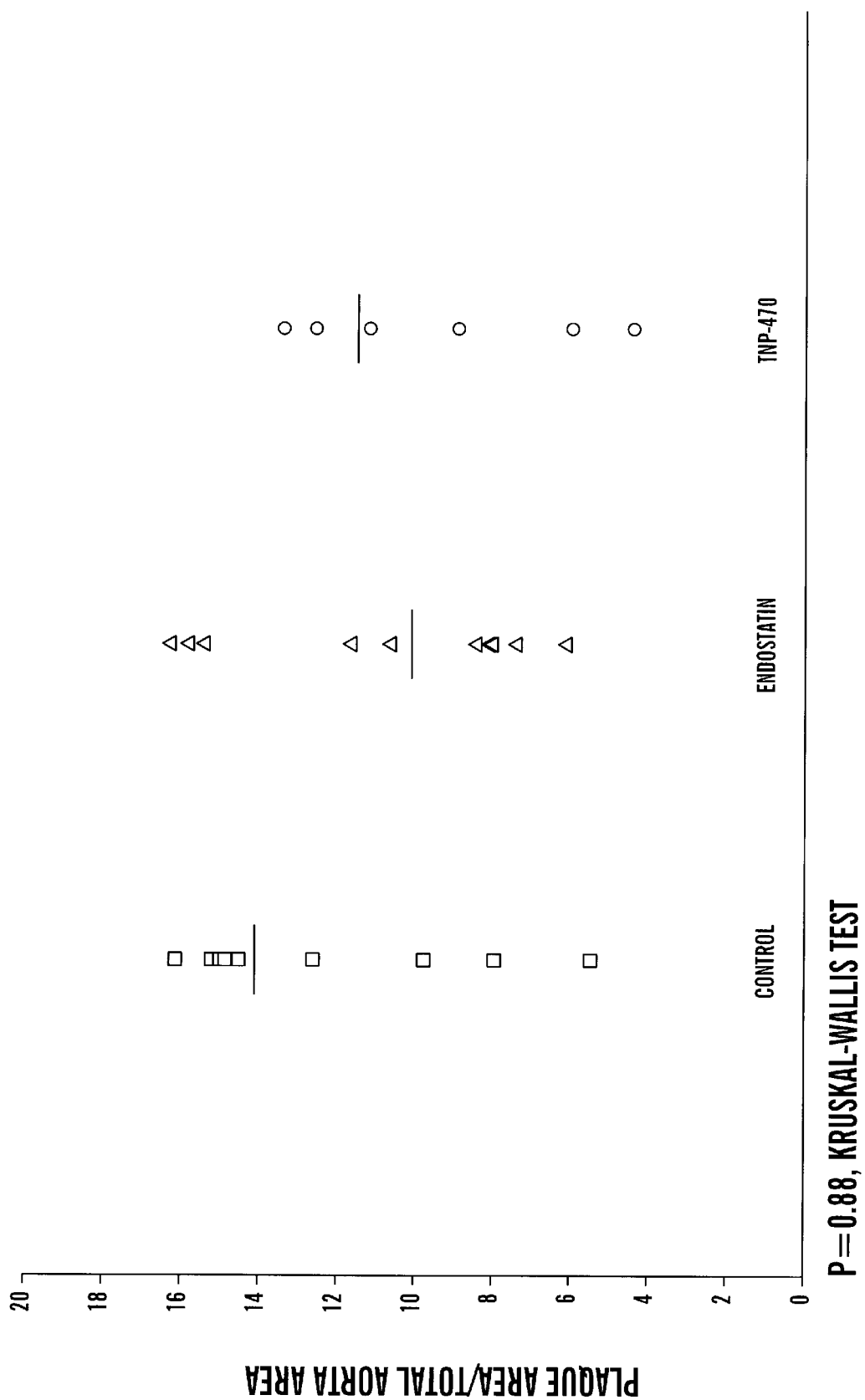

FIG. 6 shows effect of angiogenesis inhibitors on early-stage lesions in the entire aorta. The extent of atherosclerosis was measured as the percent surface area of the aorta covered with Sudan IV-positive lesions. Treatment with endostatin (triangle) or TNP-470 (circle) from age 6 to 22 weeks resulted in no significant difference in lesion severity, compared to controls (square).

DETAILED DESCRIPTION OF THE INVENTION

The present invention provides a means for treating an individual with a coronary ailment by inhibiting growth of the plaque vessels that are present in lesions associated with such cardiovascular problems. Preferably, one selects the individuals who will be treated by this method. One screens the individual for an assessment of plaque growth in order to select individuals with a potential for unstable plaques. Although not wishing to be bound by theory, we believe that individuals with unstable plaques are at higher risk for a serious vascular problem. These individuals are selected by examining criteria such as plaque neovascularization, growth, plaque size, and/or ratio of inflammatory cells. For example, measuring the intima area to the total wall area of the plaque. If the area is at least about 0.4, preferably about 0.5, more preferably 0.54 or greater, then the plaque is considered potentially unstable and the individual is selected for treatment. Analyses of human lesions show some correlation of intimal neovascularization and intimal thickness, as measured by the ratio of intima area to total wall area (intima area plus media area measured in cross section). For example, one study showed that 97% of lesions with an intima area to total wall area of less than 0.54 had no intimal capillaries, whereas 98% of plaques with intima to wall areas ratios of greater than 0.54 had microvessels (Zhang, Y., et al., *Am. J. Path.* 143: 164–72, 1993). We found such intimal vessels in about 13% of advanced lesions from Apolipoprotein E-deficient mice. The frequencies of vessels in the lesions increases nine-fold in lesions with intimal thickness that exceeds 250 microns compared to lesions with 100–250 micron thickness. Thus, plaque thickness can be a factor that can predict the presence of intimal neovascularization lesions. One can also look directly at plaque neovascularization or plaque growth by diagnostic imaging modalities MRI, ultrasound, nuclear scintigraphy etc. Plaque neovascularization can also be detected indirectly by targeting hemorrhage in the vessel wall, inflammatory cells, or proliferating cells in lesions, which are all features of atherosclerotic lesions that are spatially and temporally correlated with intimal neovascularization.

Although detailed evaluations of plaque size and intimal neovascularization does not demonstrate a strong linear correlation between both parameters, we believe they are relevant factors that can preferably be considered in selecting individuals for the present treatment. In primates, removal of an atherogenic diet resulted in a six-fold reduction of plaque blood flow but only a minimal regression of plaque size (Williams, J. K., et al., *Circ. Res.* 62: 525–23, 1988). Thus, other additional factors such as inflammatory cell contact, cell density and matrix composition of lesions are also important in regulating the development of intimal neovascularization, and can also be considered. Individuals are preferably not treated at the earliest stages of development of atherosclerosis, but rather at later stages, where the plaque is growing rapidly, has reached a critical size, and/or plaque neovascularization is occurring.

Casting studies and confocal microscopy have shown that the plaque related intimal vessels arise mostly as branches from the native adventitial vasa vasorum (Moulton, K. S., et al., *Circulation* 99: 1726–32, 1999). Some studies have shown a higher prevalence of neovascularization in lesions with plaque rupture, mural hemorrhage or unstable angina (Isner, J. M., et al., *Lancet* 348: 370–4, 1996; Baumgartner, I., et al., *Circulation* 97: 1114–23, 1998). The presence of neovascularization in plaques has a correlation with the proliferation rates of all cell types (O'Brien, E. R., *Am. J. Pathol.* 145: 883–94, 1994).

Although the capillaries within atherosclerotic lesions are too small to be detected by conventional angiography, the detection of intimal neovascularization in atherosclerotic lesions may be accomplished by known methods such as magnetic resonance imaging with contrast agents that show enhancement in tissues with increased perfusion and permeability; nuclear scintigraphy of lesions that show accumulation of technetium-99m labeled agents that target endothelial cells and/or inflammatory cells in lesions; and by intravascular, duplex, and conventional ultrasound used in conjunction with blood contrast agents (Vallabhajosula, S., J., *Nuclear Med* 38: 1788–96, 1997). Newly developed technologies such as optical coherence tomography (OCT) and infrared or rahman spectroscopy can be enhanced to detect target molecules associated with the endothelial cells that comprise plaque neovascularization or evidence of hemorrhage around the neovascularization in the plaque.

Plaque vessels are often found in areas rich in macrophages, T cells and mast cells—which are cell types that can activate angiogenesis (Kwon, H. M., et al., *J. Clin. Invest.* 101:1551–6, 1998; Williams, J. K., et al., *Circ. Res.* 62: 515–23, 1988; Folkman, J., in *Cancer Medicine,* Les & Febiger, Philadelphia, Pa., 1993). Their close proximity to inflammatory cells and expression of adhesion molecules such as VCAM-1, ICAM-1, and E-selectin in the endothelium of plaque vessels suggests that these vessels recruit inflammatory cells and initiate a positive feedback mechanism whereby both angiogenesis and the inflammatory cell contents of lesions are enhanced (Takeshita, S., et al.,*J. Clin. Invest.* 93: 662–70, 1994). It is also likely that supply of oxygen and nutrients via plaque vessels is a precondition for growth beyond a certain stage for diffusion from the artery lumen, which would be insufficient to meet the metabolic demands of the plaque.

The use of angiogenesis inhibitors in combination with cholesterol lowering agents should act in additive or synergistic form. Cholesterol lowering agents are well known in the art. For a review, see Hunninghake, D. B., *Clin. Cardiol.* 22 (Suppl.): 1144–8, 1999. Marked reduction of serum cholesterol levels after removal of an atherogenic diet resulted in a regression of plaque neovascularization. Examples of cholesterol lowering agents include the bile acid sequestrants cholestyramine and colestipol, nicotinic acid, the statins (including lovastatin, pravastatin, and simvastatin), gemfibrozil, probucol, and clofibrate.

We have found that by administering an angiogenesis inhibitor or a nucleic acid sequence encoding such inhibitor to individuals meeting the above-mentioned criteria for unstable plaques we can inhibit plaque growth and thereby inhibit lesion severity. In one preferred embodiment, one can select such individuals prior to development of a serious obstruction and the angiogenesis inhibitor can be administered as a prophylactic to prevent development of vascular ailments such as atherosclerosis, stroke, myocardial infarction, etc.

In another embodiment the obstruction is large and can reduce blood flow. Thus, it may need to be treated by an additional means (i.e., a collateral treatment) other than just treatment by an angiogenesis inhibitor. One can use any means known. For example, angioplasty. In this embodiment the angiogenesis inhibitor can be administered concurrently to assist in recovery, or subsequently, for example to inhibit development of restenosis.

Angiogenesis inhibitors are known in the art. For example U.S. Pat. Nos. 5,698,586 and 5,290,807 describe a large number of fumagillol derivatives. A particularly preferred one is O-chloroacetyl carbamoylfumagillol (referred to as AGM-1470 or TNP-470). U.S. Pat. No. 5,854,205 discusses endostatin. Other inhibitors include thalidomide (U.S. Pat. No 5,712,291), angiostatin, vasostatin, platelet factor 4, thrombospondin, IFN-α, IFN-β, etc. Endostatin and fumagillol derivatives are presently preferred.

Typically one administers the angiogenesis inhibitor itself to the individual. However, some inhibitors are proteins, fragments thereof, or peptides, e.g., endostatin, and are encoded by nucleic acid sequences. These compounds can be administered as nucleic acid molecules which will then encode the inhibitor. Preferably, the nucleic acid is administered in a form with a secretory signal present.

The signal sequence allows the antiangiogenic protein, fragment or peptide to be secreted from the cell. The signal sequence usually consists of about 16 to about 29 amino acids, starting with two or three polar residues and continuing with a high content of hydrophobic amino acids. Signal sequences are known in the art. For example, the signal peptide from the monocyte chemoattractant protein-1 (MCP-1), human interferon-cc, human gastrin-releasing peptide, human interleukin-2 (IL-2), mouse IL-3, human glucocerebrosidase, IL-7, IL-4, type I IL-1 receptor and type II IL-1 receptor (Maeda et al, *Nature* 315: 592, 1985; Lebacq-Verheyden et al *Molec. Cell. Biol.* 8: 3129, 1988; Smith et al., *Proc. Natl. Acad. Sci. USA* 82: 84804, 1985; Miyajima et al Gene 58: 273, 1987; Martia et al, *DNA* 7: 99, 1988; U.S. Pat. No. 4,965,195; IP 367,566; U.S. Pat. No. 4,968,607; and EP 460,846). Preferably, the secretory signal-angiogenesis inhibitor is constructed to contain a cleavage site between the signal sequence and the inhibitor.

We believe this approach is surprising in light of present approaches which suggest the administration of angiogenesis promoters to treat vascular injuries. See U.S. Pat. No. 5,830,879. However, while conventional revascularization procedures have clearly shown benefits in the relief of ischemic symptoms and improved exercise tolerance and lifestyle, these interventions do not always reduce mortality and morbidity from myocardial infarction and stroke in all patients. Yet, for patients with left main coronary or multiple-vessel involvement, these interventions have been shown to preserve myocardial function and survival (Hamm, C. W., et al., *N. Eng. J. Med.* 331: 1037–43, 1994; Investigators B, *N. Eng. J. Med.* 335: 217–25, 1996).

In addition, recent studies have demonstrated that angiographic evaluations of plaques do not accurately predict their tendency to cause acute ischemic syndromes. Early angiographic examinations of coronary lesions at the time of thrombolytic therapy have demonstrated that the majority of "culprit lesions" were not hemodynamically significant prior to plaque rupture, erosion, hemorrhage and thrombosis (Falk, E., et al., *Circulation* 92: 657–71, 1995). Consequently, the tightest stenosis does not necessarily confer the most risk for myocardial infarction. Therefore, it is not surprising that therapeutic strategies designed to relieve symptoms of flow-limiting stenosis have previously only had limited benefits in the prevention of acute ischemic complications.

We have discovered that it is the unstable plaques that provide the greatest risk and plaque neovascularization is a feature that renders lesions more likely to rupture, hemorrhage or cause vascular thrombosis (Tenaglia, A. N., *Amer Heart J.* 135: 10–4, 1998; Paterson, J. C., *Arch. Pathology* 25: 474–87, 1938). Thus, by screening for plaque neovascularization and assessing clinical risk factors that promote atherosclerosis, we can select individuals that have the potential for such unstable plaques. Being able to identify and target individuals with such unstable plaques is very important. Falk has shown that in many instances individuals have been treated by angioplasty and subsequently experienced significant pathology as a result of unstable plaques (*Circulation* 92: 657–71, 1995). The majority of unstable lesions were not hemodynamically significant prior to the onset of the heart attack or stroke (Falk, E., *Circulation* 92:657–71, 1995). By targeting such plaques by administration of an angiogenesis inhibitor we can inhibit plaque neovascularization, which in turn inhibits plaque growth, stabilizes the plaque and reduces the risk of ischemic complications.

For example, the treatments of Apo E-deficient mice with angiogenesis inhibitors involved a "preventative" treatment strategy and showed reduced intimal vessels in the plaques of chronically treated mice. Although these studies were not designed to show regression of established intimal vessels, this will also occur. Accordingly, angiogenesis inhibitors will inhibit endothelial cell proliferation or migration without inducing endothelial cell toxicity. While quiescent endothelium that is not proliferating may not be sensitive to all these agents, regression of such established vessels versus inhibition of new vessel formation can be accomplished in combination with other modes of treatment such as balloon catheters. The timing and duration of angiogenesis inhibitor therapy can be adjusted depending upon the condition of the patient as discussed above. For example, with atherosclerosis, angiogenesis inhibitors can be used as a preventative treatment to delay lesion progression or stabilize lesions. Ischemia is the primary condition that is necessary for the use of collaterals such as balloon catheters. When the preventative treatments can reduce plaque progression such that ischemia can be avoided, then such collateral treatment would not be needed.

To screen individuals to detect the potential for plaque instability, antibodies or some other factor specifically associated with plaques that will selectively bind to inflammatory cells or endothelial cells may be used for imaging purposes. Suitable labels include radioisotopes, iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

Suitable markers may include those that may be detected by X-radiography, NMR or MRI. For X-radiographic techniques, suitable markers include any radioisotope that emits detectable radiation but that is not overtly harmful to the patient, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99m. The labeled antibody or antibody fragment will then preferentially accumulate at the location of inflammatory cells or endothelial cells. The labeled antibody or antibody fragment can then be detected using known techniques.

Those of ordinary skill in the art will recognize that a large variety of possible moieties can be coupled to the antibodies or other molecules of the invention. See, for example, "Conjugate Vaccines", *Contributions to Microbiology and Immunology*, J. M. Cruse and R. E. Lewis, Jr (eds.), Carger Press, New York, 1989, the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents (see Killen and Lindstrom, *J. Immunol.* 133:1335–2549, 1984; Jansen, F. K., et al., *Imm. Rev.* 62:185–216, 1982; and Vitetta et al., supra).

Preferred linkers are described in the literature. See, for example, Ramakrishnan, S., et al., *Cancer Res.* 44: 201–208 (1984), describing the use of MBS (M-maleimidobenzoyl-N-hydroxysuccinimide ester). See also Umemoto et al., U.S. Pat. No. 5,030,719, describing the use of a halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido] hexanoate (Pierce Chem. Co, Cat #21651 G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfosuccinimide: Pierce Chem. Co., Cat. #24510) conjugated to EDC.

The inhibitors are present in pharmaceutically acceptable compositions. Those compositions include those suitable for oral, rectal, intravaginal, topical, nasal, ophthalmic or parenteral administration, all of which may be used as routes of administration using the materials of the present invention. Other suitable routes of administration include direct injection onto an arterial surface and intraparenchymal injection directly into targeted areas of an organ. Compositions suitable for parenteral administration are preferred. The term "parenteral"includes subcutaneous injections, intravenous, intramuscular, intrasternal injection or infusion techniques.

The compositions may conveniently be presented in unit dosage form and may be prepared by any of the methods well known in the art of pharmacy. Methods typically include the step of bringing the active ingredients of the invention into association with a carrier which constitutes one or more accessory ingredients.

Compositions of the present invention suitable for oral administration may be presented as discrete units such as capsules, cachets, tablets or lozenges, each containing a predetermined amount of the nucleic acid and/or polypeptide of the invention in liposomes or as a suspension in an aqueous liquor or non-aqueous liquid such as a syrup, an elixir, or an emulsion.

Preferred compositions suitable for parenteral administration conveniently comprise a sterile aqueous preparation of the molecule of the invention which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Oral agents provide the advantages of easy administration and chronic systemic treatment. However, local delivery of angiogenesis inhibitors via catheters, gene transfer techniques, and endovascular stents or polymers is presently preferred in order to control localized disease.

If desired, the DNA or RNA, preferably DNA, may also be used with a microdelivery vehicle such as cationic liposomes and adenoviral vectors. For a review of the procedures for liposome preparation, targeting and delivery of contents, see Mannino and Gould-Fogerite, *Bio Techniques,* 6: 682, 1988). See also, Feigner and Holm, *Bethesda Res. Lab. Focus,* 11: 21, 1989; and Maurer, R. A., *Bethesda Res. Lab. Focus,* 11: 25, 1989.

Replication-defective recombinant adenoviral vectors can be produced in accordance with known techniques (Quantin, et al., *Proc. Natl. Acad. Sci. USA,* 89: 2581–2584, 1992; Stratford-Perricadet, et al., *J. Clin. Invest.,* 90: 626–630, 1992; and Rosenfeld, et al., *Cell,* 68: 143–155, 1992).

The injured portion of the blood vessel is contacted with the nucleic acid sequence encoding an angiogenesis inhibitor by any means familiar to the skilled artisan, including, for example, by syringe, double-balloon catheters, porous-balloon catheters and hydrophilic coated balloon catheters (Jorgensen, et al., *Lancet* 1:1106–1108, 1989; Wolinsky, et al., *J. Am. Coll. Cardiol.,* 15:475–485, 1990; March, et al., *Cardio Intervention,* 2:11–26, 1992; WO93/00051, WO93/00052; U.S. Pat. No. 5,304,121; Dichek, *Textbook of interventional Cardiology,* Vol. 2, 61:989–1005).

A hydrophilic coated balloon catheter is preferred in certain situations. A hydrophilic coated balloon catheter has a hydrophilic polymer on the outer surface of the balloon which permits the contact between the hydrophilic polymer bearing the nucleic acid to be transferred and the cells of the injured portion of the blood vessel to be made with some pressure, thus facilitating the transfer of the nucleic acid to the cells. However, other supports for the hydrophilic polymer are also useful, such as catheters or solid rods having a surface of hydrophilic polymer. Preferably, the catheters or rods or other substrates are flexible, to facilitate threading through the arteries to reach the point of intended application. Preferably, the hydrophilic polymer is a hydrogel polymer, a cross-linked polymer material formed from the combination of a colloid and water. Cross-linking reduces solubility and produces a jelly-like polymer that is characterized by the ability to swell and absorb liquid, e.g., that containing the DNA. Suitable hydrogel polymers include, for example, those selected from the group consisting of polycarboxylic acids, cellulosic polymers, gelatin, polyvinylpyrrolidone, maleic anhydride polymers, polyamides, polyvinyl alcohols, and polyethylene oxides. Preferred hydrogels are polyacrylic acid polymers available as HYDROPLUS (Mansfield Boston Scientific Corp., Watertown, Mass.) and described in U.S. Pat. No. 5,091,205.

When a hydrophilic arterial balloon is used, it is not necessary to protect the balloon prior to inflation, since relatively little of the nucleic acid is lost in transit to the treatment site until the balloon is inflated and the hydrophilic polymer bearing the nucleic acid is pressed against the injured site. When hydrophilic polymer-surfaced catheters or rods are used as the vehicle or substrate, the surface can protected, e.g. by a sheath, until the point of intended application is reached, and then the protection removed to permit the hydrophilic polymer bearing the nucleic acid to contact the site where the plaques are present.

The nucleic acid in aqueous solution is incorporated into the hydrophilic polymer to form a nucleic acid-hydrophilic polymer composition. The nucleic acid is incorporated without complexing or chemical reaction with the hydrophilic polymer, and is preferably relatively freely released therefrom when placed in contact with the cells at the site of injury. The resulting structure comprises a support, e.g. the balloon of the balloon catheter, on which is mounted the hydrogel, in or on which is incorporated the desired DNA and its associated vehicle, e.g., phage or plasmid vector. The hydrophilic polymer is preferably adhered to the support, so that after application of the DNA to the target cells, the hydrophilic polymer is removed with the support.

Preferably, the nucleic acid-hydrophilic composition contacts the arterial cell by means of a catheter. The catheter is preferably a balloon catheter constructed for insertion in a blood vessel and has a catheter shaft and an expandable dilation balloon mounted on the catheter shaft. At least a portion of the exterior surface of the expandable portion is defined by a coating of a tenaciously adhered hydrophilic polymer. Incorporated in the hydrophilic polymer is an aqueous solution of the DNA to be delivered to the cells of the injured portion of the blood vessel.

In general, when dry, the hydrophilic polymer (preferably hydrogel) coating is preferably on the order of about 1 to 10 microns thick, with a 2 to 5 micron coating typical. Very thin hydrogel coatings, e.g., of about 0.2–0.3 microns (dry) and much thicker hydrogel coatings, e.g., more than 10 microns (dry), are also possible. Typically, hydrogel coating thickness may swell by about a factor of 2 to 10 or more when the hydrogel coating is hydrated.

Procedures for preparing and using a balloon with a hydrogel coating are set forth in U.S. Pat. No. 5,304,121, the disclosure of which is incorporated herein by reference.

Oral agents such as thalidomide, TNP-470 and various metalloprotease inhibitors are in clinical trials for the treatment of cancer and macular degeneration. In some instances, these inhibitors of angiogenesis also have additional drug activities that could be beneficial in the treatment of atherosclerosis. Thalidomide is an inhibitor of angiogenesis with known effects on immune function that are employed to treat transplant rejection and the erythema nodosa reaction of leprosy (D'Amato, R. J., et al., *Proc. Natl. Acad. Sci. USA* 91: 4082–5, 1994; Tamura, F., et al., *Transplantation* 49: 20–5, 1990). Metalloprotease inhibitors may reduce plaque angiogenesis but also alter the collagen content of lesions and promote plaque stability. Angiogenesis inhibitors such as TNP-470 inhibit smooth muscle cell proliferation in vitro and therefore should reduce smooth muscle cell content in atherosclerotic lesions (Koyama, H., et al., *Circ. Res.* 79: 757–64, 1996)

An exemplary pharmaceutical composition is a therapeutically effective amount of a molecule that will inhibit angiogenesis as shown in a standard assay such as the chick chorioallantoic membrane (CAM) assay (Crum, et al., *Science* 230: 1375, 1985), which optionally is included in a pharmaceutically-acceptable and compatible carrier. The term "pharmaceutically-acceptable and compatible carrier" as used herein, and described more fully below, includes (i) one or more compatible solid or liquid filler diluents or encapsulating substances that are suitable for administration to a human or other animal, and/or (ii) a system, such as a retroviral vector, capable of delivering the nucleic acid molecule to a target cell. In the present invention, the term "carrier" thus denotes an organic or inorganic ingredient, natural or synthetic, with which the molecules of the invention are combined to facilitate application. The term "therapeutically-effective amount" is that amount of the present pharmaceutical composition which produces a desired result or exerts a desired influence on the particular condition being treated. For example, the amount necessary to inhibit angiogenesis of plaque vessels to provide prophylactic protection. Typically when the composition is being used as a prophylactic additional doses will be administered at periodic intervals after the initial administration. Various concentrations may be used in preparing compositions incorporating the same ingredient to provide for variations in the age of the patient to be treated, the severity of the condition, the duration of the treatment and the mode of administration.

The term "compatible", as used herein, means that the components of the pharmaceutical compositions are capable of being commingled with a small molecule, nucleic acid and/or polypeptides of the present invention, and with each other, in a manner such that does not substantially impair the desired pharmaceutical efficacy.

The angiogenesis inhibitor molecules, when used for administration, are prepared under aseptic conditions with a pharmaceutically acceptable carrier or diluent.

Doses of the pharmaceutical compositions of the invention will vary depending on the subject and upon the particular route of administration used. Dosages can range from 0.1 to 100,000 $\mu$g/kg per day, more preferably 1 to 10,000 $\mu$g/kg. By way of an example only, an overall dose range of from about, for example, 1 microgram to about 300 micrograms might be used for human use. This dose can be delivered at periodic intervals based upon the composition. For example, preferably spaced apart about every other day. Other compounds might be administered daily. Pharmaceutical compositions of the present invention can also be administered to a subject according to a variety of other, well-characterized protocols. For example, using pulsed therapy. This is a technique where the amount and timing of dosages is varied as opposed to regular intervals at the same dosage. Desired time intervals for delivery of multiple doses of a particular composition can be determined by one of ordinary skill in the art employing no more than routine experimentation.

The molecules, DNA sequences, proteins or peptides of the invention may also be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof and are not excluded from the scope of this invention. Such pharmaceutically acceptable salts include, but are not limited to, those prepared from the following acids: hydrochloric, hydrobromic, sulfuric, nitric, phosphoric, maleic, acetic, salicylic, p-toluene-sulfonic, tartaric, citric, methanesulfonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical compositions, for medical use, which comprise nucleic acid and/or polypeptides of the invention together with one or more pharmaceutically acceptable carriers thereof and optionally any other therapeutic ingredients.

One can also administer the nucleic acid molecules encoding an angiogenesis inhibitor. The DNA or RNA sequences encoding these peptides such as endostatin or proteins can readily be made by known techniques. These DNA sequences can be administered to a host animal by numerous methods including vectors such as viral vectors, naked DNA, adjuvant assisted DNA catheters, gene gun, liposomes, etc. In one preferred embodiment the DNA sequence is administered to a human host as either a prophylactic or therapeutic treatment to inhibit angiogenesis. One can administer cocktails containing multiple angiogenesis inhibitors.

Vectors include chemical conjugates such as those described in WO 93/04701, which has a targeting moiety (e.g. a ligand to a cellular surface receptor) and a nucleic acid binding moiety (e.g. polylysine), a viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include herpes virus vectors such as a herpes simplex I virus (HSV) vector (Geller, A. I. et al., *J. Neurochem* 64: 487, 1995; Lim, F. et al., in *DNA Cloning: Mammalian Systems*, D. Glover, Ed., Oxford Univ. Press, Oxford England, 199); Geller, A. I., *Proc. Natl. Acad. Sci.* USA 90: 7603, 1993; Geller, A. I., I *Proc. Natl. Acad. Sci* USA 87: 1149, 1990), adenovirus vectors (LeGal LaSalle et al., Science 259: 988, 1993; Davidson, et al., *Nat. Genet* 3: 219, 1993; Yang, et al., *J. Virol.* 69: 2004, 1995), and adeno-associated virus vectors (Kaplitt, M. G., et al., *Nat. Genet.* 8:148, 1994). The DNA sequence would be operably linked to a promoter that would permit expression in the host cell. Such promoters are well known in the art and can readily be selected.

Stabilized forms of these complexes can readily be made, for example, by conjugates such as a poly(alkylene oxide) conjugate. The conjugate is preferably formed by covalently bonding the hydroxyl terminals of the poly(alkylene oxide) and the angiogenesis inhibitor in a manner not to effect the angiogenic inhibiting action. Other art recognized methods of conjugating these materials include amide or ester linkages. Covalent linkage as well as non-covalent conjugation such as lipophilic or hydrophilic interactions can be used.

The conjugate can be comprised of non-antigenic polymeric substances such as dextran, polyvinyl pyrrolidones, polysaccharides, starches, polyvinyl alcohols, polyacryl amides or other similar substantially non-immunogenic polymers. Polyethylene glycol (PEG) is preferred. Other poly(alkylenes oxides) include monomethoxy-polyethylene glycol polypropylene glycol, block copolymers of polyethylene glycol, and polypropylene glycol and the like. The polymers can also be distally capped with C1–4 alkyls instead of monomethoxy groups. The poly(alkylene oxides) used must be soluble in liquid at room temperature. Thus, they preferably have a molecular weight from about 200 to about 20,000 daltons, more preferably about 2,000 to about 10,000 and still more preferably about 5,000.

One can administer these stabilized compounds to individuals by a variety of means as discussed above.

We have demonstrated that plaque vessels and intimal neovascularization promotes the progression of atherosclerosis, and demonstrated by treatment with angiogenesis inhibitors that we were able to reduce plaque growth.

EXAMPLES

The fumagillin analogue TNP-470 is a selective inhibitor of endothelial cell proliferation and migration and is under investigation in clinical trials as an anticancer agent. TNP-470 inhibits primary tumor growth and demonstrates 70% inhibition of angiogenesis in the corneal micropocket assay (Ingber, D., et al., *Nature* 348: 555–7, 1990). Endostatin, a C-terminal 20 kd fragment of the basement membrane protein Collagen XVIII, is a potent inhibitor of primary tumor growth and endothelial cell proliferation and migration (Boehm, T., et al., *Nature* 390: 404–7, 1997; O'Reilly, M. S., et al., *Cell* 88: 277–85, 1997).

We first demonstrate that intimal capillaries occur in advanced lesions of Apolipoprotein E deficient (Apo E-/-) mice by immunohistochemistry with antibodies against CD31 and von Willebrand factor (vWf) and by transmission electron microscopy (TEM). We then show that chronic treatment with recombinant murine endostatin or TNP-470 significantly reduces the further growth of atherosclerosis without affecting levels.

Methods

1. Animals and Experimental Design

Male Apo E-/-mice (Jackson Labs, Bangor Me.) were fed a 0.15% cholesterol diet (Western Type #88137, Teklad) from age 6–8 weeks. At 20 weeks of age, ten animals were sacrificed to evaluate the baseline extent of atherosclerosis. The remaining littermates were divided into three groups and treated for 16 weeks as follows: 1) recombinant murine endostatin at 20 mg/kg per day by subcutaneous (s.c.) injection, a dose shown to produce over 95% inhibition of primary tumor growth in mice (Boehm, T., et al., *Nature* 390: 404–7, 1997); 2) the fumagillin analogue TNP-470 at 30 mg/kg s.c. every other day; 3) control animals received a similar volume of saline (TNP-470 buffer) or PBS (endostatin buffer).

After 16 weeks of treatment, animals were euthanized with methoxyflurane. A blood sample was obtained from the right ventricle for the analysis of serum cholesterol, performed by an automated calorimetric assay on a Hitachi 917 instrument (Children's Hospital, Boston, Mass.). The heart and aorta were perfusion-fixed with 2% paraformaldehyde and dissected as described (Palinski, W., et al., *Arterioscler. Thromb.* 14: 605–16, 1994; Tangirala, R. K., et al., *J. Lipid Res.* 36:2320–8, 1995). Atherosclerotic plaques in the aortas were used for histology and plaque areas were only determined at the aortic origin (Paigen, B., et al., *Artherosclerosis* 68: 231–40, 1987). However, to document the extent of disease in the total aorta, the unopened aortas were photographed.

The effects of these angiogenesis inhibitors on late stage lesions were then compared to their effects on early lesions, in which intimal vessels were rarely observed. Animals were treated with endostatin or TNP-470 from age 32 to 48 weeks (late-stage experiment) or from 6 to 22 weeks (early-stage experiment). Plaque involvement was measured at the aortic origin. Since the aortas from early stage animals were not used for immunohistochemistry in these experiments, the extent of atherosclerosis was also measured in the entire aorta (percent surface area of Sudan IV stained-lesions; Paliniski, W., et al., *Arteriosclr. Thromb.* 14: 605–16, 1994).

Animal health and weight was monitored throughout treatment. The percentages of animals available for analysis in all studies were 92% (range 86–100), 89% (80–94), and 91% (86–100) for the endostatin, TNP-470, and control groups, respectively. Chronic dermatitis and dental malocclusion were the most common reasons for exclusion.

2. Immunohistochemistry

To detect intimal capillaries, the hearts and portions of the descending aorta with substantial lesions were embedded in paraffin, sectioned (10 μm), digested with 0.02% protease XXIV (Sigma) for 6 minutes at room temperature, and incubated with rabbit polyclonal anti-human vWf antibody (Dako, Carpinteria, Calif., 1:500 dilution) or rat monoclonal anti-mouse CD31 antibody (Pharmigen, San Diego, Calif., 20 Tg/ml). When acetone-fixed frozen sections were stained, the CD31 antibody was used at 5 Tg/ml. The bound antibodies against vWf or CD31 were detected with biotinylated goat anti-rabbit or rabbit anti-rat (mouse absorbed) antibodies (Vector, Burlinghame, Calif., 1:250 dilution) and the avidin-biotin peroxidase complex (ABC standard kit, Vector). A red reaction product was produced with 3-amino-9-ethyl carbazole substrate (AEC, Dako) and sections were counterstained with Gill's hematoxylin (Sigma). Vascular sections incubated with non-immune serum served as negative controls. Positive staining of the endothelium on the lumen and in adventitial capillaries served as an internal control. Intimal vessels were identified under high power (400×) and counted when both an endothelial cell nucleus and lumen were seen and when the vessel was also observed in an adjacent section.

Smooth muscle cells were identified with a monoclonal IgG2a antibody against human smooth muscle cell I actin (Dako, M0851; Nakashima, Y., et al, *Arteriocler. Thromb.* 14: 133–40, 1994). Sections were immersed in 0.1 M sodium citrate, pH 6.0 and heated for 10 minutes in the microwave. Primary antibody was bound to sections at 3 Tg/ml and then visualized with biotinylated anti-mouse IgG2a antibody (1:200 dilution, Amersham RPN1181) and the ABC method described above. The adjacent medial layer of vessels served as positive control.

3. Transmission Electron Microscopy

Aortas with atherosclerotic lesions were isolated from retired breeder APO E-/-mice that were fed the Western diet for 20 weeks. Extensive lesions in the descending aorta were divided transversely into two segments. One segment was frozen and cryosectioned for CD31 immunohistochemistry; the other was processed for TEM. Only lesions that screened positive for intimal vessels were analyzed on an EM 10 electron microscope (Zeiss, Oberkochen, Germany).

4. Recombinant Murine Endostatin and TAP-470 Treatments

Recombinant murine endostatin was prepared as described using the expression plasmid TBO1 #8 transformed into the E. coli strain BL21: DE3 (Boehm, T., et al., *Nature* 390: 404–7, 1997; O'Reilly, M. S., et al., *Cell* 88: 277–85, 1997). Induction results in a fusion protein with the amino acid sequence MARRASVGTDHHHHHH (SEQ ID NO:1) at the N-terminus followed by the sequence of endostatin, which corresponds to the C-terminal, 184 amino acids of mouse collagen XVIII. Murine endostatin was purified under denaturing conditions on a $Ni^{+2}$-NTA column (QiaExpressionist Handbook, Qiagen). Purity was analyzed by SDS-PAGE. Prior to use in Apo E-/-mice, endostatin batches were tested for inhibition of Lewis Lung Carcinoma growth in C57BI6/J mice (Boehm, T., et al., *Nature* 390: 404–7, 1997).

The Apo E-/-mice received 20 mg/kg of endostatin subcutaneously every day. Animals tolerated the injections and showed regular weight gain, activity levels, and no ulceration at the injection sites.

The fumagillin analogue TNP-470 was provided for these studies by TAP Holdings, Deerfield Ill. An injection solution of TNP-470 (3 mg/ml) was freshly prepared and mice received 30 mg/kg subcutaneously every other day. Control animals received a similar volume of saline or endostatin buffer.

5. Plaque Morphometry

Plaque Area. To determine the extent of atherosclerosis at the aortic origin, 40 serial sections (8–10 Tm thickness) of the aortic sinus were collected on 10 slides (Paigen, B., et al., *Artherosclerosis* 68: 231–40, 1987). Every second slide was stained with hematoxylin and eosin for morphometry. The rest were used for immunohistochemistry to count intimal vessels and determine intimal smooth muscle cell contents. Plaque images were captured at 100× magnification with a Hitachi HV-C20 3CCD digital camera and measured with the Leica Q500MC image analysis program (Dong, Z. M., et al., *J. Clin. Invest.* 102: 145–52, 1998). Lesion area for each animal was reported as the mean intimal cross-sectional area ($mm^2$). In the early-stage experiment, plaque involvement in the entire aorta was also measured by image analysis as the percentage of aortic surface area covered with lesions (Tangiala, R. K., et al., *J. Lipid. Res.* 36: 2320–8, 1995; Dong, Z. M., et al., *J. Clin. Invest.* 102: 145–52, 1998)

Plaque cell density. Cell densities in aortic sinus plaques were evaluated to determine if endostatin or TNP-470 treatments affected lesion cellularity. Cell nuclei in the intima of the aortic sinus plaques were counted at three mid-lesion levels (slides 4, 6, and 8). Cell density was reported as the number of cells per intimal area (cells/$mm^2$).

Intimal smooth muscle cell content. To determine if angiogenesis inhibitor treatments affected smooth muscle cell migration or proliferation in lesions, two slides from the middle of the aortic sinus were stained for smooth muscle cell α actin. For each animal, the number of intimal smooth muscle cells and total cell nuclei were counted in 8 non-overlapping fields. A smooth muscle cell was counted only if it stained for smooth muscle cell α actin and its cell nucleus was seen. The mean percentage of smooth muscle cells relative to total cells was determined for each animal.

6. Statistical Analysis

The inhibitory effects on median plaque growth induced by chronic treatment with TNP-470 and endostatin were compared using the Kruskal-Wallis test. Data presented in Table I and II were evaluated using the Fisher's exact test. Intimal cell density and smooth muscle cell content of lesions from animals in treatment and control groups were compared using nonparametric ANOVA analysis with adjustment for multiple measurements from each animal (Table III).

Results

Apo E-/-Mice Have Intimal Neovascularization

Figure 1A:
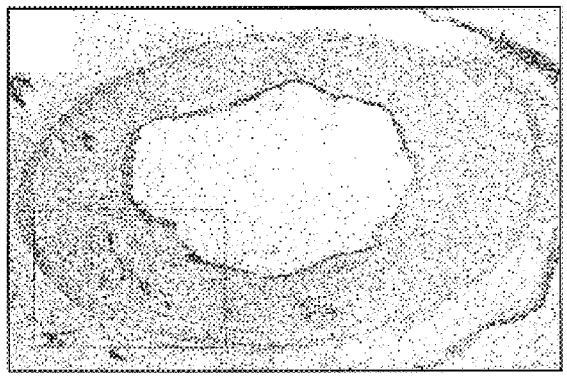
FIGS. 1A–F show intimal neovascularization in advanced lesions of Apo E-/-mice.
Figure 1B:
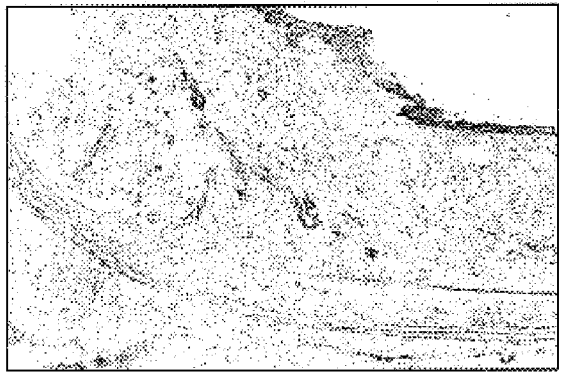
Figure 1C:
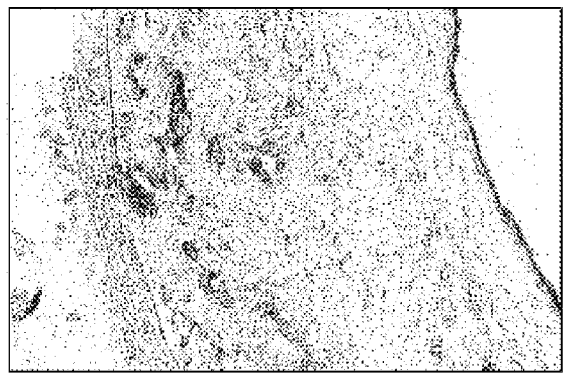
Figure 1D:
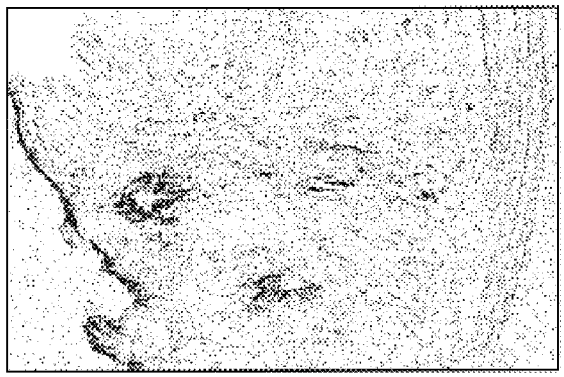
Figure 1E:
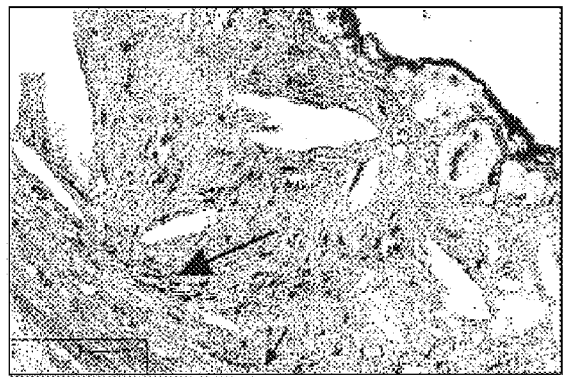
Figure 1F:
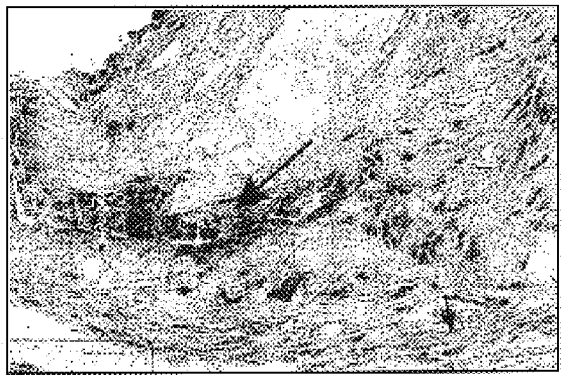

Advanced atherosclerotic lesions of Apo E-/-mice were first examined for the presence of intimal capillaries. Intima vessels were identified by immunohistochemistry with antibodies against the endothelial cell markers CD31 (FIGS. 1A–D) or vWf (FIGS. 1E–F). Thin-walled capillary-like vessels were observed in lesions harvested from the descending aorta (FIGS. 1A–E) and the aortic sinus (FIG. 1F). Intimal neovascularization was also observed when advanced atherosclerotic lesions were examined by TEM (FIG. 2A). Increased numbers of capillaries (FIG. 2b) and endothelial cells with signs of early lumen formation (FIG. 2C) are seen in the adventitia adjacent to atherosclerotic lesions.

The incidence of lesions with intimal vessels was generally low in Apo E-/-mice but increased in more extensive lesions. No vessels were observed in fatty streak lesions and a few in lesions less than 250 $\mu$m thick. Intimal vessels were detected in 15 of 114 (13%) advanced aortic lesions from cholesterol-fed Apo E-/-mice ages 36–60 weeks (Table I). The majority of plaques that contained intimal vessels (13/15, 87%) were more than 250 $\mu$m thick. The incidence of intimal vessels in this group was increased 9-fold compared to 100–250 $\mu$m thick lesions ($P \leq 0.0005$).

Plaque Growth is Reduced by Chronic Treatment with Endostatin or TNP-470

Apo E-/-mice were treated with an angiogenesis inhibitor, either endostatin or TNP-470, for a prolonged period. A chronic treatment schedule was chosen due to the uncertainty for the onset of neovascularization in murine lesions. Based on our initial survey of mice younger than 20 weeks, plaques thicker than 250 $\mu$m were infrequent. We therefore induced substantial atherosclerosis by feeding Apo E-/-mice a diet that contained 0.15% cholesterol and at 20 weeks initiated treatments for 16 weeks.

The median (range) aortic origin plaque area in 10 mice sacrificed at baseline was 0.250 mm$^2$ (0.170–0.348, N=10) and is represented as the dashed line in FIG. 3. The remaining three groups of animals were treated with endostatin, TNP-470 and buffer as described in Methods. The median plaque areas were 0.321 mm$^2$ (0.238–0.412, N=10), 0.402 mm$^2$ (0.248–0.533, N=15), and 0.751 mm$^2$ (0.503–0.838, N=12) for the endostatin, TNP-470, and control groups, respectively ($P \leq 0.0001$). Despite the considerable variability in plaque areas, there was little overlap between the treatment and control groups (FIG. 3). Since the extent of lesions before treatment was 0.250 mm2, chronic treatment with endostatin or TNP-470 appeared to inhibit plaque growth by 85% and 70%, respectively. Percent inhibition calculated by the formula: [100] [1-(median plaque area treated −0.25)/(median plaque area control −0.25)].

The cholesterol levels in treatment and reference groups were not different (FIG. 4). Median cholesterol levels at the time of sacrifice were 877 (range 542–1045, N=10), 823 (461–1164, N=15), and 918 mg/dl (558–1366, N=12) in the endostatin, TNP-470 and control groups, respectively (P=0.62). In a subset of animals, cholesterol levels were similar before and after 4 weeks of treatment.

The median weights after treatment were 36 g (31–37), 31 g (24–34), and 35 g (26–49) for the endostatin, TNP-470, and control groups. All animals increased weight during treatment, but TNP-470-treated animals gained only 4 g (P=0.001) compared to 8 g for control and 9 g for endostatin-treated animals.

Significant inhibitions of plaque growth by endostatin and TNP-470 were also observed in a second experiment that treated mice from 20 to 36 weeks. Median plaque areas were 0.475 mm$^2$ (0.308–0.598, N=12), 0.370 mm$^2$ (0.181–0.521, N=12) and 0.690mm$^2$ (0.591–0.720, N=12) for the animals in the endostatin, TNP-470 and control groups (P=0.001).

For these experiments, plaque measurement at the aortic origin was selected to detect a change in plaque thickness rather than surface area. However, photographed images of the entire aorta, taken before the aortas were dissected for histology, also demonstrated a noticeable reduction of plaque surface area in endostatin or TNP-470-treated animals (not shown).

Inhibition of Plaques by Endostatin or TNP-470 is Less Prominent in Early Lesions It was then evaluated whether endostatin or TNP-470 were similarly effective in animals with predominantly advanced lesions as in animals with predominantly early lesions. In this experiment cholesterol-fed Apo E-/-mice were treated with endostatin or TNP-470 from age 32 to 48 weeks. Plaque areas at the aortic origin were determined after the same 16-week treatment period (FIG. 5). Median plaque areas for the endostatin, TNP-470 and control groups were 0.422 mm$^2$ (0.283–0.637, N=12), 0.448 mm$^2$ (0.260–0.566, N=14), and 0.584 mm$^2$ (0.426–0.911, N=13), respectively. The inhibitions of plaque growth were smaller than in the previous experiments but still significant (P=0.002). Again, cholesterol levels were similar in all groups (P=0.13). Final weights were 39 g (32–50), 33 g (25–37), and 35 g (32–44) for the endostatin, TNP-470 and control mice (first level test $P \leq 0.0001$; TNP-470 vs control P=0.003; endostatin vs control P=0.04, not significant by adjusted P value 0.017).

The effect of endostatin and TNP-470 treatment was then evaluated in mice that had mostly early lesions without significant intimal neovascularization. Apo E-/-mice were started on diet at 6 weeks and divided into endostatin, TNP-470, and control groups. After treatment for 16 weeks, lesions in the entire aorta were not very extensive and no significant difference was seen between treatment and control groups (FIG. 6, P=0.88). Median percent plaque areas were 9.6% (6.2–16.4, N=10), 11.7% (4.4–16.6, N=8), and 14.4% (5.4–16.1, N=12) for the endostatin, TNP-470 and control animals, respectively. Plaque measurements at the aortic origin also showed no difference (not shown). Therefore, the inhibitory effects of endostatin and TNP-470 were less pronounced during early atherogenesis.

The Incidence of Intimal Vessels in Endostatin or TNP-470 Treated Lesions is Reduced Aortic sinus plaques isolated from control and treated animals were examined for the presence of intimal vessels. The percentage of plaques that contained any intimal vessels was significantly smaller in treated mice (5% for endostatin, P=0.032; 0% for TNF-470, P=0.003) compared to 29% of controls (Table II).

Smooth Muscle Cell Content and Cellular Density of Lesions

The magnitude of plaque inhibition observed with endostatin and TNP-470 raised the possibility that these agents not only affect plaque angiogenesis, but may also affect other cell types found within atherosclerotic lesions. To evaluate if TNP-470 and endostatin influence smooth muscle cell migration and proliferation in atherosclerotic lesions, the smooth muscle cell contents of lesions from treatment and control mice were compared (Table III). The median smooth muscle cell contents of aortic sinus lesions from control mice were 20.4% and were similar for endostatin (19.4%, P=0.20) and TNP-470 treated mice (19.8%, P=0.55).

The cellular density of atherosclerotic lesions from treated and control mice were determined at three levels of the aortic sinus as described in Methods. The calculated median cell densities were similar between the control and TNP-470 groups, but were increased in the endostatin group (1645 cells/mm$^2$, P$\leq$0.0005).

Atherosclerotic lesions in the aorta of Apo E-/-mice contain intimal vessels, as do human lesions. This observation is remarkable because the absolute dimensions of murine lesions are much smaller. The incidence of intimal vessels in advanced murine lesions was 13%, whereas the incidence in human lesions has been reported at 40–53% (O'Brien, E. R., et al., *Am. J. Path.* 145: 883–94, 1994). Prior studies showed infrequent vasa vasorum in normal mouse aortas. Comparisons of the lamellar structure across many species suggested that a minimal vessel wall thickness was required for the presence of vasa vasorum (Wolinsky, H., et al., *Circ. Res.* 20: 99–111, 1967). Intravital studies of tissue oxygenation in tumors demonstrated that significant hypoxia and acidosis occur when the distance from a capillary exceeds 100 $\mu$m (Torres Filho, J., et al., *Proc. Natl. Acad. Sci. USA* 91: 2081–5, 1994). Given the thin media of the murine aorta, only relatively large lesions may exceed the limit where growing plaques require additional sources of perfusion beyond the artery lumen and adventitial vessels.

Our results are consistent with this. However, the intimal thickness of many plaques from Apo E-/-mice exceeded 100 $\mu$m, but only 13% of these lesions showed intimal neovascularization. The metabolic requirements of plaque tissues may depend on lesion composition and differ from tumors. In addition, the contribution from adventitial vessels was not measured.

The vessel density in vascularized plaques ranged from 1–17 capillaries per high power field, but the vessel number in these lesions did not correlate with intimal thickness. For example, one plaque (FIG. 1A) had over 30 vessels and a maximal intimal thickness of 312 $\mu$m, whereas a lesion with 486 $\mu$m thickness (not shown) had 8–10 capillaries. It is likely that factors other than size such as cell density, leukocyte infiltrates, and matrix composition also influence the development of plaque vessels. Despite this lack of a linear correlation, plaque size may appear to be an indicator for the presence of intimal vessels because their incidence in lesions >250 $\mu$m was increased 9-fold compared to smaller lesions.

The observation of intimal vessels in lesions from Apo E-/-mice provided a model for testing whether potent angiogenesis inhibitors affect the progression of atherosclerosis in these animals. The results of two separate experiments conducted on animals treated from age 20 to 36 weeks showed significant inhibition of atherosclerosis without affecting cholesterol levels (FIG. 3). Compared to animals sacrificed at baseline, endostatin or TNP-470 treatments inhibited atherosclerosis by 85% and 70%, respectively. In the second experiment, either treatment significantly inhibited plaque growth, but the degree of inhibition by endostatin was less than that by TNP-470.

Significant inhibition of plaque growth by endostatin or TNP-470 were seen even when the treatment was delayed until 32 weeks, although the degree of inhibition was smaller (FIG. 5). One potential explanation for the smaller inhibition could be that the plaque growth rate from 20 to 36 weeks is different than from 32 to 48 weeks. Second, both endostatin and TNP-470 are reversible inhibitors of endothelial cell proliferation and appear to exert few effects on quiescent non-proliferating endothelium (O'Reilly, M. S., et al., Cell 88: 277–85, 1997; Budson, A. E., et al., *Biochem. Biophys. Res. Commun.* 225: 141–5, 1996). Therefore, the effects of these inhibitors on plaques with established intimal vessels may be different than on plaques that develop intimal neovascularization during the treatment period.

Interestingly, we saw little effect when treatments were performed during early stages of atherosclerosis (FIG. 6). In Apo E-/-mice fed the Western diet, fatty streaks are typically seen from 8–20 weeks and plaques with smooth muscle cells are initially observed at 15 weeks[19]. Our results therefore suggest that endostatin or TNP-470 did not significantly affect foam cell and early fibromuscular lesions.

When lesions from endostatin or TNP-470-treated animals were examined, few intimal vessels were observed. However, this correlation does not conclusively prove that inhibition of plaque growth occurred because intimal neovascularization was decreased. The reduced neovascularization could merely be a consequence of reduced plaque size, rather than an effect of angiogenesis inhibitors and the cause of reduced atherosclerosis.

The process of atherosclerosis involves multiple factors that control inflammation, cell proliferation and migration, cholesterol metabolism, and interactions between cells, blood and matrix. It is possible these agents altered functional characteristics of the endothelium, which influence leukocyte adhesion, transmigration, or activation. TNP-470 has been shown to enhance E-selectin expression, but this would not be predicted to inhibit lesion development (Budson, A. E., et al., *Biochem. Biophys. Res. Commun.* 225: 141–5, 1996). Smooth muscle cell proliferation and migration are inhibited by TNP-470 in vitro, but require doses that are 30 to 70-fold greater than the doses for endothelial cells (Ingber, D., et al., *Nature* 348: 555–7, 1990; Koyama, H., et al., *Circ. Res.* 79: 757–64, 1996). Despite these in vitro findings, no significant differences in the smooth muscle cell contents of lesions from treated and control animals were observed in the present study.

Currently, only limited information on the mechanism of action of TNP-470 and endostatin is available. TNP-470 regulates cyclin activity in endothelial cells and forms a covalent bond to methionine aminopeptidase-2, a cobalt-dependent metallotprotease (Sin, N., et al., *Proc. Natl. Acad. Sci. USA* 94: 6099–103, 1997; Abe, J., et al., *Cancer Res.* 54:3407–12, 1994). Further investigations of the mechanisms of action for TNP-470 and endostatin may therefore provide insights towards understanding their effects on plaque growth.

The combined findings indicate that intimal vessels contribute to the progression of atherosclerosis. First, similar actions of atherosclerosis were observed with two very different agents that share a potent inhibitory effect on endothelial cell proliferation. Second, the inhibition of plaque growth by these agents was associated with a decreased incidence of intimal neovascularization. Lastly, these inhibitors showed little effect during early stages of plaque development when intimal neovascularization was unlikely to occur.

The endothelium of plaque vessels may have qualitative differences from the arterial endothelium that covers the plaque.

All references described herein are incorporated herein by reference.

TABLE I

Intimal Vessels in Advanced Lesions

| Max-intimal depth | Vessel (+) | Vessel (−) | Plaque total | Incidence |
|---|---|---|---|---|
| >250 microns | 13 | 33 | 46 | 0.2826 |
| 100–250 microns | 02 | 66 | 68 | 0.0294 |
| Total | 15 | 99 | 114 | 0.1316 |

P ≦ 0.0005, Fisher's exact test

TABLE II

Intimal neovascularization in control and angiogenesis-inhibitor treated lesions.

| Treatment | Aortic Sinus Plaque (#) | Neovascularization (+)* | P value** |
|---|---|---|---|
| Control | 24 | 7 (29%) | |
| Endostatin | 22 | 1 (5%) | 0.032 |
| TNP-470 | 27 | 0 | 0.003 |

*Plaques with at least one intimal capillary were counted positive (see Methods).
**Fisher's exact test

TABLE III

Intimal Smooth Muscle Content and Cell Density of Lesions

| Treatment | SMC (%) | P value* | Cell Density (cells/mm$^2$) | P value* |
|---|---|---|---|---|
| Control (N = 12) | 20.4 (14.3–30.5) | — | 1183 (867–1640) | — |
| Endostatin (N = 10) | 19.4 (16.2–22.7) | 0.20 | 1646 (962–2361) | ≦0.0005 |
| TNP-470 (N = 15) | 19.8 (14.6–23.5) | 0.55 | 1261 (855–1926) | 0.22 |

Median values and (range of values for individual animals) are listed.
*Compared to control using nonparametric ANOVA.

What is claimed:

1. A method of stabilizing a vascular plaque comprising administering an effective amount of an angiogenesis inhibitor to an individual, in need thereof, wherein the angiogenesis inhibitor is a fumagillol derivative.

2. The method of claim 1, wherein the angiogenesis inhibitor fumagillol derivative is o-chloroacetyl carbamoyl-fumagillol.

3. The method of claim 1, wherein the angiogenesis inhibitor is administered by using a catheter.

* * * * *

SEQUENCE LISTING

<160> NUMBER OF SEQ ID NOS: 1

<210> SEQ ID NO 1
<211> LENGTH: 16
<212> TYPE: PRT
<213> ORGANISM: Murinae gen. sp.

<400> SEQUENCE: 1

Met Ala Arg Arg Ala Ser Val Gly Thr Asp His His His His His His
1               5                   10                  15